United States Patent [19]
Reznikoff et al.

[11] Patent Number: 6,159,736
[45] Date of Patent: Dec. 12, 2000

[54] METHOD FOR MAKING INSERTIONAL MUTATIONS USING A TN5 SYNAPTIC COMPLEX

[75] Inventors: William S. Reznikoff; Igor Y. Goryshin, both of Madison, Wis.

[73] Assignee: Wisconsin Alumni Research Foundation, Madison, Wis.

[21] Appl. No.: 09/159,363

[22] Filed: Sep. 23, 1998

[51] Int. Cl.[7] .......................... C12N 15/63; C12N 15/87; C12N 15/74

[52] U.S. Cl. ................... 435/455; 435/461; 435/462; 435/463; 435/471; 435/473

[58] Field of Search .................... 435/455, 461, 435/462, 463, 471, 473

[56] References Cited

U.S. PATENT DOCUMENTS

| | | | |
|---|---|---|---|
| 5,679,560 | 10/1997 | Ligon et al. | 435/183 |
| 5,925,545 | 7/1999 | Reznikoff et al. | 435/69.2 |
| 5,948,622 | 9/1999 | Reznikoff et al. | 435/6 |
| 5,965,443 | 10/1999 | Reznikoff et al. | 435/473 |

FOREIGN PATENT DOCUMENTS

| | | |
|---|---|---|
| 98/10077 | 3/1998 | WIPO . |
| WO 98/10077 | 3/1998 | WIPO . |

OTHER PUBLICATIONS

Lu et al., "Characterization of the Interaction Between the Tn7 Transposase (TnsA+B) and the Transposase Regulator TnsC", Keystone Symposia: Transposition and Site–Specific Recombination, Santa Fe (1997).

Mizuuchi, Kiyoshi, "In Vitro Transposition of Bacteriophage Mu: A Biochemical Approach to a Novel Replication Reaction," *Cell*, 35:785–794 (1983).

Morisata, Donald, et al., "TN10 Transposition and Circle Formation In Vitro," *Cell*, 51:101–111 (1987).

Morita et al., "Nested Deletions from a Fixed Site as an Aid to Nucleotide Sequencing: An in vitro System Using Tn3 Transposase", *DNA Research*, 3: 431–433 (1996).

Pues et al., "Construction of a Deletion Library Using a Mixture of 5'–Truncated Primers for Inverse PCR (IPCR)", *Nucleic Acids Research*, 25(6): 1303–1304 (1997).

Sakai, Janice, et al., "Identification and characterization of a pre–cleavage synaptic complex that is an early intermediate in TN10 transposition," *The EMBO Journal*, 14(17):4374–4383 (1995).

Strathmann, et al., "Transposon–facilitated DNA Sequencing", *Proc. Natl. Acad. Sci.*, 88: 1247–1250 (1991).

Tomacsanyi et al. "Intramoleclar Transposition by a Synthetic IS50 (Tn5) Derivative", *J. Bacteriology*, 172(11): 6348–6354 (1990).

Wang et al., "Inversions and Deletions Generated by a Mini–γ (Tn1000) Transposon", *J. of Bacteriology*, 176(5): 6348–6354 (1990).

Wang et al., "pDUAL: A Transposon–Based Cosmid Cloning Vector for Generating Nested Deletions and DNA Sequencing Templated in vivo", *Proc. Natl. Acad. Sci.*, 90: 7874–7878 (1993).

Weinreich, Michael D., "A Functional Analysis of the TN5 Transposase: Identification of Domains Required for DNA Binding and Multimerization," *J. Mol. Biol.*, 241:166–177 (1994).

(List continued on next page.)

*Primary Examiner*—Kenneth R. Horlick
*Attorney, Agent, or Firm*—Quarles & Brady LLP

[57] ABSTRACT

A method for making insertional mutations at random or quasi-random locations in the chromosomal or extra-chromosomal nucleic acid of a target cell includes the step of combining, in the target cell, cellular nucleic acid with a synaptic complex that comprises (a) a Tn5 transposase protein and (b) a polynucleotide that comprises a pair of nucleotide sequences adapted for operably interacting with Tn5 transposase and a transposable nucleotide sequence therebetween, under conditions that mediate transpositions into the cellular DNA. In the method, the synaptic complex is formed in vitro under conditions that disfavor or prevent the synaptic complexes from undergoing productive transposition.

18 Claims, 2 Drawing Sheets

Synaptic complex transformation transposon and transposase form synaptic complex in vitro competent cells deliver complex into cells select for the library of insertions

OTHER PUBLICATIONS

Yohda et al., "Solid–Phase Nested Deletion: A New Subcloning–less Method for Generating Nested Deletions", *DNA Research,* 2: 175–181 (1995).

Zhu and Marshall, "Rapid Construction of Nested Deletions of Recombinant Plasmid DNA for Dideoxy Sequencing", *BioTechniques,* 18(2): 222–224 (1995).

Ahmed, Asad, "Use of Transposon–Promoted Deletions in DNA Sequence Analysis", *Letter to Editor in J.Mol. Biol.,* 178: 941–948 (1984).

Benjamin, Howard W., "Excision of Tn10 from the donor site during transposition occurs by flush double–strand cleavages at the transposon termini," *Proc. Natl. Acad. Sci. USA,* 89:4648–4652 (May 1992).

Craigie, Robert, et al., "A defined system for the DNA strand–transfer reaction at the initiation of bacteriophage Mu transposition: Protein and DNA substrate requirements," *Proc. Natl. Acad. Sci. USA,* 82:7570–7574 (Nov. 1985).

de la Cruz, Norberto B., et al., "Characterization of the TN5 Transposase and Inhibitor Proteins: a Model for the Inhibition of Transposition," *Journal of Bacterioilogy,* 175(21):6932–6938 (Nov. 1993).

Devine et al., "Efficient Integration of Artificial Transposons into Plasmid Target in vitro: a Useful Tool for DNA Mapping, Sequencing and Genetic Analysis", *Nucleic Acid Research,* 22 No. 18: 3765–3772 (1994).

Devine et al., "A Transposon–base Strategy for Sequencing Repetitive DNA in Eukaryotic Genomes", *In Press, Genome Research* (1998).

Hattori et al., "A Novel Method for Making Nested Deletions and Its Application for Sequencing of a 300 kb Region of Human APP Locus", *Nucleic Acids Research,* 25 No. 9: 1802–1808 (1997).

Henikoff, Steven, "Unidirectional Digestion with Exonuclease III Creates Targeted Breakpoints for DNA Sequencing", *Gene,* 28: 351–359 (1984).

Jilk, Ross A., et al., "The Organization of the Outside End of Transposon Tn5," *Journal of Bacteriology,* 178(6):1671–1679 (Mar. 1996).

Jilk et al., "Implications of Tn5–Associated Adjacent Deletions", *J. of Bacteriology,* 175: 1264–1271 (1993).

Krishnan et al., "Construction of a Genomic DNA 'Feature Map' by Sequencing from Nested Deletions: Application to the HLA Class I Region", *Nucleic Acids Research,* 23 No. 1: 117–122 (1995).

Lavoie, B.D., et al., "Transposition of Phage Mu DNA," Current Topics in Microbiology and Immunology, Dept. of Biochemistry, U. of Western Ontario.

Junop et al., EMBO J. 15(10), 2547–2555 (1996).

Mizuuchi et al., Cell 70, 303–311 (1992).

Weinert et al., Cold Spring Harbor Symp. Quant. Biol. 49, 251–260 (Abstract Only) (1984).

Goryshin et al., "Tn5 in Vitro Transposition," *The Journal of Biological Chemistry* 273:7367–7374 (1998).

Goryshin et al., "Insertional transposon mutagenesis by electroporation of released Tn5 transposition complexes," *Nature Biotechnology* 18:97–100 (2000).

Junop et al., "Multiple roles for divalent metal ions in DNA transposition: distinct stages of Tn10 transposition have different $Mg^{2+}$ requirements," *The EMBO Journal* 15:2547–2555 (1996).

Leschziner, et al., "Tn552 transposase catalyzes concerted strand transfer in vitro," *Proc. Natl. Acad. Sci. USA* 95:7345–7350 (1998).

Mizuuchi et al., "Assembly of the Active Form of the Transposase–Mu DNA Complex: A Critical Control Point in Mu Transposition," *Cell* 70: 303–311 (1992).

Park et al., "In Vitro Transposition of Tn5," *J. Korean Soc. Microbiol.* 27:381–389 (1992).

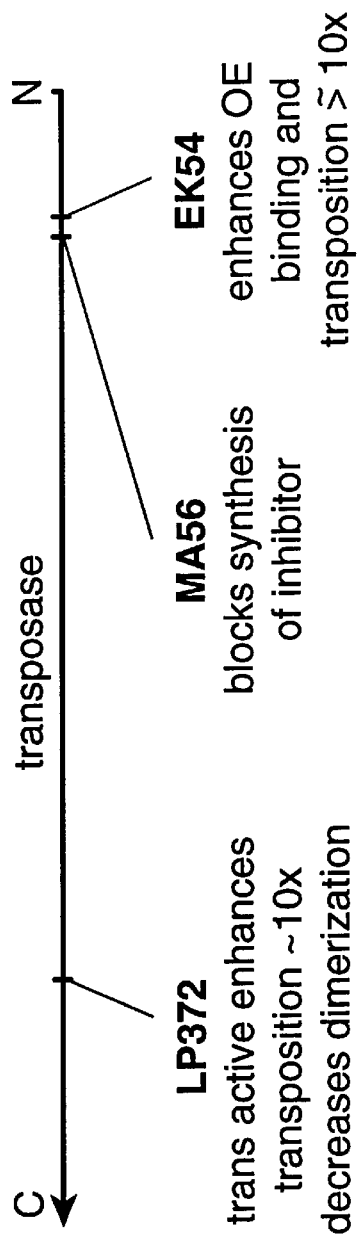
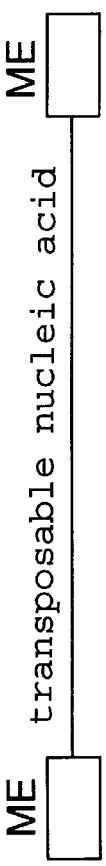
FIG 2
FIG 3
```
          1                            19
OE     CTGACTCTTATACACAAGT
MOSAIC CTGTCTCTTATACACATCT
IE     CTGTCTCTTGATCAGATCT
```
FIG 4

METHOD FOR MAKING INSERTIONAL MUTATIONS USING A TN5 SYNAPTIC COMPLEX

STATEMENT REGARDING FEDERALLY SPONSORED RESEARCH OR DEVELOPMENT

This invention was made with United States government support awarded by the following agencies: NIH Grant No.: GM50692 and NSF Grant No.: 9419784. The United States has certain rights in this invention.

CROSS-REFERENCE TO RELATED APPLICATIONS

Not applicable.

BACKGROUND OF THE INVENTION

Efficient insertion of exogenous nucleic acid into the chromosomal and extra-chromosomal nucleic acid of cells is desired in the art of molecular biology to identify chromosomal regions involved in expressing or regulating expression of peptides and proteins. This same technology is also advantageously used in developing new therapeutic and pharmacologic agents.

One common method relies upon in vivo Tn5 mutagenesis to insert polynucleotides of interest into cellular DNA and to construct libraries of cells that contain inserted polynucleotides at random or quasi-random locations. Existing in vivo Tn5 mutagenesis methods require target cells to encode transposase, either natively or from an introduced expression construct. Accordingly, it can be necessary to construct a suitable expression system appropriate to each target cell type. This can be time consuming, and requires extensive knowledge of the requirements of each target cell type.

In many cases, the gene that encodes transposase is encoded by an active transposon, which can continue to transpose in a target cell after the initial desired mutagenesis step. Such undesired residual transposition is undesired in that it complicates the analysis of insertional mutant libraries.

Furthermore, many techniques for in vivo Tn5 mutagenesis rely upon a complex biological mechanism for introducing exogenous DNA into the target cells, such as bacteriophage lambda transducing phage or a conjugating plasmid. It would be desirable to avoid requiring such complex biological systems.

Shoji-Tanaka, A., et al., *B.B.R.C.* 203:1756–1764 (1994) describe using purified retroviral integrase to mediate gene transfer into murine cells.

Kuspa, A. and W. F. Loomis, *P.N.A.S. U.S.A.* 89:8803–8807 (1992) and others have described specifically integrating a plasmid linearized with a restriction enzyme into a genomic restriction site by electroporating enzyme-cut nucleic acid along with the cleaving enzyme into target cells.

BRIEF SUMMARY OF THE INVENTION

The present invention is summarized in that a method for efficiently inserting a transposable polynucleotide at random or quasi-random locations in the chromosomal or extra-chromosomal nucleic acid of a target cell includes the step of combining, in the target cell, cellular nucleic acid with a synaptic complex that comprises (a) a Tn5 transposase protein complexed with (b) a polynucleotide that comprises a pair of nucleotide sequences adapted for operably interacting with Tn5 transposase and a transposable nucleotide sequence therebetween, under conditions that mediate transpositions into the cellular DNA. In the method, the synaptic complex is formed in vitro under conditions that disfavor or prevent the synaptic complexes, which are poised for transposition, from actually undergoing productive transposition. The frequency of productive transposition of the transposable nucleotide sequence into the target nucleic acid can be enhanced by using in the method either a hyperactive transposase or a transposable polynucleotide that comprises sequences particularly well adapted for efficient transposition in the presence of Tn5 transposase, or both.

The present invention is further summarized in that a method for forming library of cells that comprise insertional mutations includes the steps of combining in a plurality of target cells the cellular nucleic acid with the synaptic complex as described, and screening for cells that comprise insertional mutations.

In another aspect, the invention is further summarized as a library of cells that comprise insertional mutations formed according to the above-mentioned method. Such populations of cells that comprise random and independent mutational insertions in their genomes can be screened to select those cells that comprise an insertional mutation that induces a phenotypic or genotypic change relative to cells that were not subject to insertional mutagenesis.

It is an advantage of the present invention that the transposable polynucleotides used to form synaptic complexes can consist of transposon DNA apart from any flanking sequences. This is advantageous in that it reduces the likelihood of intramolecular transposition and increases the likelihood of transposition into a target genome. Moreover, eliminating donor backbone (DBB) sequences from the polynucleotide simplifies preparation of the transposon sequences that can be used in the method.

It is another advantage of the present invention that the synaptic complex can form under conditions that disfavor non-productive intramolecular transposition events. This is advantageous in that substantially all of the synaptic complexes can undergo transposition when combined with the cellular DNA. Little, if any, of the nucleic acid in the synaptic complexes is inactive.

It is a feature of the present invention that transposition-promoting conditions are encountered only after the synaptic complex is in the presence of the target nucleic acid in the target cell.

Other objects, advantages, and features of the present invention will become apparent upon consideration of the following detailed description.

BRIEF DESCRIPTION OF THE SEVERAL VIEWS OF THE DRAWINGS

FIG. 2 a preferred transposase enzyme for use in the method.

FIG. 3 depicts transposon terminal sequences that can be used in the transposable polynucleotide sequence in the present invention. The OE sequence is identified on the accompanying sequence listing as SEQ ID NO.: 1, the IE sequence is SEQ ID NO.: 2 and the mosaic sequence is SEQ ID NO.: 3.

FIG. 4 depicts a transposon or transposable polynucleotide sequence having mosaic ends and a transposable nucleic acid sequence therebetween.

DETAILED DESCRIPTION OF THE INVENTION

Figure 1:
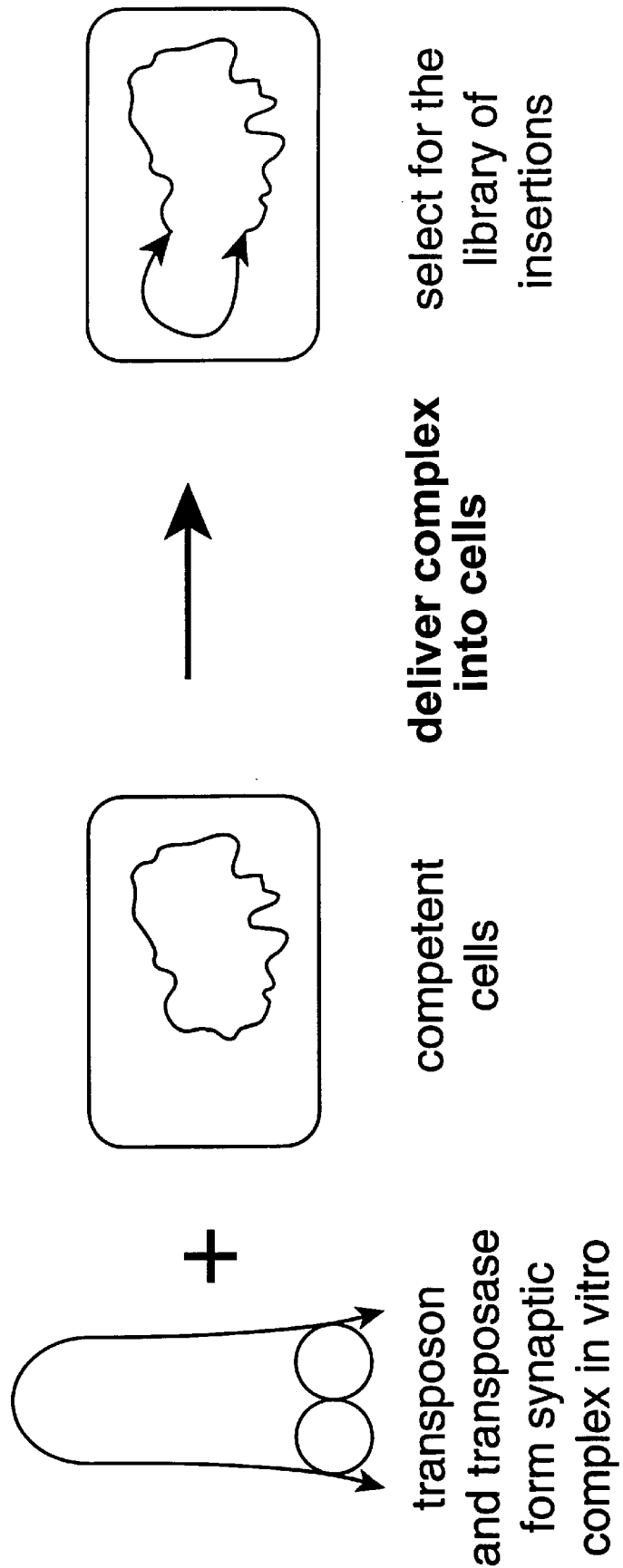
FIG. 1 depicts the transfer of a synaptic complex into a target cell followed by selection of insertion mutants.

In a system for in vitro transposition using modified Tn5 transposase described in International Application No. PCT/US97/15941 (International Publication No. WO 98/10077), incorporated herein by reference in its entirety, the applicants demonstrated productive transposition of a transposable polynucleotide in vitro using a modified mutant Tn5 transposase and modified Tn5 polynucleotide sequences flanking a transposable nucleotide sequence.

The present invention differs from the prior system in that in the present invention synaptic complexes are formed in vitro, although in vitro transposition is substantially absent. Rather, the synaptic complexes are introduced into target cells whereupon transposition in vivo readily occurs. FIG. 1 presents a schematic view of one aspect of the present Tn5-based method for efficiently introducing insertional mutations at random or quasi-random locations in the chromosomal or extra-chromosomal nucleic acid of a target cell. In the method, cellular nucleic acid in a target cell is combined with a synaptic complex that comprises (a) a Tn5 transposase protein (shown as a pair of adjacent circles in FIG. 1) and (b) a polynucleotide that comprises a pair of inverted nucleotide sequences (shown as arrows in FIG. 1) adapted for operably interacting with Tn5 transposase and a transposable nucleotide sequence therebetween, under conditions that mediate transpositions into the cellular DNA. The synaptic complex structure is an intermediate in the transposition of the transposable polynucleotide into the cellular nucleic acid. It is herein disclosed that one can separate synaptic complex formation from transposition by interfering with the ability of the synaptic complex to participate in a polynucleotide strand transfer reaction. In the method, the synaptic complex is formed in vitro under conditions that disfavor or prevent the synaptic complexes from undergoing productive transposition. The invention can expand the use of Tn5 mutagenesis methods to, for example, bacteria that are not close relatives of E. coli and for which little is known about the structures of, and other requirements for, promoters and other regulatory sequences. In such cells, transposase may not be expressed in adequate amount, or may be unstable. The present method avoids the need to produce an endogenous transposase molecule. Moreover, since the introduced transposase is integrally complexed with the transposon polynucleotide, it is poised to act in the presence of any target DNA and, as such is sufficiently stable to facilitate transposition of the polynucleotide with which it is complexed. One method discovered by the inventors to prevent the synaptic complexes from undergoing polynucleotide strand transfer is achieved by reducing or eliminating magnesium ions ($Mg^{++}$) from the reaction mixture. Thus, in a preferred embodiment of the method, a suitable transposase and a suitable transposable DNA element are combined in an in vitro reaction where the reaction mixture contains magnesium at a level insufficient to support polynucleotide strand transfer, or more preferably, a mixture free of magnesium ions. A suitable reaction buffer for forming the synaptic complexes can be the reaction buffer described on page 19 of the incorporated international application, modified to remove the magnesium acetate. One can also remove the BSA and spermidine from the reaction buffer. The tRNA can be eliminated from the buffer, unless nucleases are present in the reaction, in which case the tRNA can be added. It may be possible to further simplify the reaction buffer. A typical reaction is described below in the example.

The synaptic complexes are poised to mediate efficient transposition and can be advantageously placed in cold storage until needed. The synaptic complexes can be introduced into suitable target cells capable of providing conditions favorable for transposition, whereupon efficient transposition occurs. By introducing the synaptic complexes into a plurality of suitable target cells and selecting those cells that comprise insertional mutations, a library of cells that comprise random or quasi-random insertional mutations can be produced. To prepare a library of insertional mutants, the transposable nucleic sequence preferably contains a convenient selectable marker such as a gene that confers antibiotic resistance, so that cells lacking an insertional mutation in their cellular DNA can be readily distinguished from those in which productive transposition has occurred. Libraries formed according to the method can be screened for genotypic or phenotypic changes after transposition. At the molecular genetic level, one can employ standard analytical methods including hybridization, restriction fragment mapping, nucleotide sequencing, and combinations thereof, or other methods to identify genetic changes. At the phenotypic level, one can evaluate members of a library of transposition mutants for individual mutants having an altered growth property or other phenotype.

A kit of synaptic complexes comprising transposable polynucleotide sequences having desired characteristics, such as those described below, can be commercialized to facilitate rapid preparation of libraries comprising insertional mutations, wherein the inserted sequences have been designed to accomplish a particular goal, as described below. The synaptic complexes of the present invention are substantially free of polynucleotide molecules that have undergone productive transposition. Furthermore, because the synaptic complexes are prepared in an in vitro reaction, the complexes can be provided as a substantially pure preparation apart from other proteins, genetic material, and the like.

The Tn5 transposase in the synaptic complexes can be a Tn5 transposase that forms synaptic complexes efficiently in vitro (e.g., about 25% or more of the transposon DNA is converted into synaptic complexes with the transposase). The transposase can be a hyperactive Tn5 transposase such as that disclosed in International Application No. PCT/US97/15941. A preferred mutant Tn5 transposase is a mutant Tn5 transposase modified relative to a wild-type Tn5 transposase, the mutant transposase comprising a mutation at position 54, and a mutation at position 372, the mutant transposase having greater avidity for Tn5 outside end repeat sequences of a donor DNA and a lesser ability to form multimers than wild-type Tn5 transposase. A mutation at position 54 that confers a greater avidity for Tn5 outside end repeat sequences is a mutation from wild-type glutamic acid to lysine. A mutation at position 372 that causes a reduced ability to form non-productive multimers is a mutation from wild-type lysine to proline.

It is also preferred that the transposase be free of the so-called inhibitor protein, a protein encoded in partially overlapping sequence with the transposase which can interfere with transposase activity. In the method, the transposase is used in purified, or partially purified, form, and if the transposase enzyme is obtained from cells (using conventional methods) it may be possible to separate the transposase from the inhibitor protein before use in the method. However, it is also possible to genetically eliminate the possibility of having any contaminating inhibitor protein present by simply removing its start codon from the gene that encodes the transposase.

An AUG in the wild-type Tn5 transposase gene that encodes methionine at transposase amino acid 56 is the first codon of the inhibitor protein. However, it has already been shown that replacement of the methionine at position 56 has no apparent effect upon the transposase activity, but at the same time prevents translation of the inhibitor protein, thus resulting in a somewhat higher transposition rate. Wygand, T. W. and W. S. Reznikoff, "Characterization of Two Hyper-transposing Tn5 Mutants," *J. Bact.* 174:1229–1239 (1992), incorporated herein by reference. In particular, the present inventors have replaced the methionine with an alanine in the preferred embodiment (and have replaced the methionine-encoding AUG codon with an alanine-encoding GCC). A preferred transposase of the present invention therefore includes an amino acid other than methionine at amino acid position 56, although this change can be considered merely technically advantageous (since it ensures the absence of the inhibitor protein from the in vitro system) and not essential to the invention (since other means can be used to eliminate the inhibitor protein from the in vitro system). Shown schematically in FIG. 2 is a preferred transposase enzyme having mutations at positions 54, 56 and 372 relative to wild type Tn5 transposase.

The transposable polynucleotide in the synaptic complexes is characterized as a nucleotide sequence flanked by a pair of inverted polynucleotides that comprise an 18 or 19 base long sequence that can function in an in vitro Tn5 transposition system. The polynucleotide (or any portion thereof) can be synthesized using methods well known to those skilled in the art, or can be prepared using methods for genetically engineering nucleic acid fragments. Referring now to FIG. 3, the known nucleic acid sequence of an outside end (OE) terminal sequence of a wild-type Tn5 transposon sequence (5'-CTGACTCTTATACACAAGT-3') (SEQ ID NO.: 1) can be used as the flanking polynucleotides, as can a terminus of an inside end (IE) terminal sequence of a wild-type Tn5 transposon sequence (5'-CTGTCTCTTGATCAGATCT-3') (SEQ ID NO.: 2). Although the wild-type OE terminus sequence can be used, the inventors have demonstrated that transposition frequencies at least as high as, and typically significantly higher than, that of wild-type OE can be achieved if the termini in a construct are mosaics intermediate between OE and IE sequences. Preferred mosaic terminus sequences include bases ATA at positions 10, 11, and 12, respectively, as well as the nucleotides in common between wild-type OE and IE (e.g., at positions 1–3, 5–9, 13, 14, 16, and optionally 19). The nucleotides at position 4, 15, 17, and 18 can correspond to the nucleotides found in those positions in either wild-type OE or wild-type IE. It is noted that the transposition frequency can be enhanced over that of wild-type OE if the nucleotide at position 4 is a T, when in combination with the above-noted nucleotides. Preferred mosaic sequences include CTGTCTCTTATACACATCT (SEQ ID NO:3) and CTGTCTCTTATACAGATCT (SEQ ID NO:4). Combinations of non-identical ends can also be employed.

The transposable polynucleotide is preferably a linear polynucleotide comprising at its termini the inverted polynucleotide sequences required for Tn5 transposition. It is also possible, but less preferred, to employ a transposable polynucleotide that is linear but which comprises sequences other than the transposable nucleic acid and the inverted polynucleotide sequences. Such additional sequences can be located to either side of the transposable polynucleotide, although this arrangement is less preferred because it complicates preparation of transposon DNA. Some transposition can occur when the transposable polynucleotide is provided on a circular, supercoiled DNA molecule, although the transposition frequency is not as high as when the transposable sequence is a linear molecule.

The transposable nucleic acid sequence between the required end sequences can include any sequence that is desirably inserted into a target genome. FIG. 4 shows a schematic transposon having so-called mosaic ends and a transposable polynucleotide sequence therebetween. One skilled in the art can readily construct a desired transposable nucleic acid sequence to accomplish a particular goal. The invention is not limited to any particular nucleic acids between the inverted polynucleotide sequences. Rather, the sequence can be any detectable sequence, or a sequence that encodes a product that can be detected using methods known to those skilled in the art. By way of non-limiting example, the transposable nucleic acid sequence can provide the target cell with a selectable marker, which can be a peptide or protein encoded by the transposable nucleic acid sequence. The sequence can encode a protein that confers antibiotic resistance to a cell. Alternatively, the transposable polynucleotide can comprise a sequence whose presence can be detected in target cells. Such a sequence can include a cleavage sequence for a rare restriction enzyme, or any sequence for which a probe exists.

The transposable polynucleotide can also include sequences that regulate expression (transcription or translation) of nearby sequence. The regulatory sequences can facilitate expression of a protein or peptide encoded by a coding sequence in the transposable polynucleotide. Alternatively, the transposable polynucleotide can include regulatory sequences apart from any coding sequence or coding sequences apart from any regulatory sequence. In the former case, transposition events upstream from genomic coding sequences can provide the regulatory elements necessary to modulate transcription and/or translation of an endogenous coding sequence. In the later case, the transposed sequence can reveal previously unknown regulatory sequences in the genome by introducing a marker gene whose product is produced only when the gene is transposed to a position adjacent to a regulatory sequence in the cellular nucleic acid.

Once formed from the above-identified components in vitro, the synaptic complex can be introduced into target cells using methods known to those of ordinary skill in the art. The synaptic complexes can alternatively be stored in advance of use, for example, at −40° C. A preferred method for introducing the synaptic complex into the cell is electroporation, for example, using the example of Dauer, W. J. et al, *Nucleic Acids Research,* 16:6127 (1988), incorporated herein by reference in its entirety. Transposition follows delivery into the cellular nucleic acid without additional intervention. If the synaptic complexes are present in a volume greater than a few microliters, it is also preferred to dialyze the synaptic complexes against a low-salt buffer, e.g., without limitation, 6 mM Tris, pH 7.5 with 7–10% glycerol, before use in an electroporation reaction to reduce salts in the reaction mixture to a level sufficiently low that they do not cause arcing between the electrodes. Other suitable methods for introducing the synaptic complexes into target cells are known and can include transformation, transfection, and liposome-mediated methods.

The system provides a method for introducing mutations into cells quickly and efficiently. Because the transposable polynucleotide sequence is provided, the system is not host-specific, and should work in any target cell. The invention finds particular utility in cells, particularly bacterial cells, that do not encode transposase, since the required transposase molecule is provided directly as part of the synaptic complex. The method is demonstrated to work in non-nucleated target systems, such as bacterial cells. In particular, the synaptic complexes have been introduced into *E. coli* cells (strain MG1655) and productive transposition has been observed. No scientific impediment is known to exist that would prevent use of the method in nucleated cells, such as archaebacteria, plant and animal cells, especially cells of nematodes, amphibians, and mammals, including, but not limited to, rodents and humans. In methods for introducing synaptic complexes into nucleated cells, it may be preferable to provide a nuclear localization signal on the synaptic complex, preferably as part of a genetically modified transposase protein.

The present invention will be more readily understood upon consideration of the following example which is exemplary and is not intended to limit the scope of the invention.

EXAMPLE

In a reaction of 1 µl, 0.05 µg of a purified hyperactive transposase (EK45/MA56/LP372), the amino acid sequence of which is reported in incorporated International Application No. PCT/US97/15941, was combined with 0.1 µg of a transposable polynucleotide comprising an expression cassette that encodes a protein that confers kanamycin resistance upon a target cell. The expression cassette was flanked by the mosaic ends described in the same incorporated International Application and shown in FIG. 3. The polynucleotide was provided, in separate reactions, as a supercoiled plasmid, a linearized plasmid, or as a polynucleotide fragment comprising at its termini inverted sequences required for transposition mediated by Tn5 transposase.

The mixture was incubated for one hour in the presence or absence of magnesium ions ($Mg^{++}$) in the reaction buffer noted above. In the absence of magnesium ions, synaptic complexes form, but no transposition occurs in vitro.

After incubation, the reaction mixture was mixed with 40 µl of *E. coli* strain MG1655 and subjected to electroporation according to the incorporated method of Dauer. The cells ($1.4 \times 10^9$) were plated on LB-Kan plates and kanamycin resistant colonies were counted. When 10 µl of reaction mix was used, the mix was dialyzed into a suitable buffer to prevent arcing between the electrodes.

TABLE 1

| | Tn5 Synaptic Complex electroporation/transposition | | | |
|---|---|---|---|---|
| DNA | Tnp | $Mg^{++}$ | volume | $Kan^4$ CFU |
| supercoiled* | − | + | 1 µl | None |
| supercoiled* | + | + | 1 µl | $1.6 \times 10^3$ |
| linearized* | + | + | 1 µl | $6.9 \times 10^3$ |
| released element (PvuII cut) | + | + | 1 µl | $3.9 \times 10^3$ |
| released element | + | − | 1 µl | $5.3 \times 10^4$ |
| released element | + | − | 1 µl (dialyzed) | $4.0 \times 10^4$ |
| released element | + | − | 10 µl (dialyzed) | $5.5 \times 10^5$ |

*contained donor backbone sequences

It is apparent from the table that transposition of the transposable polynucleotide that confers kanamycin resistance upon a cell is high when the reaction mixture is incubated in the absence of magnesium ions. Superior transposition was observed when the transposable polynucleotide contains no sequences flanking the transposable portion ("released element"). A greater than 10 fold reduction in kanamycin resistant CFUs was observed when magnesium was added to the reaction mixture, presumably as a result of non-productive intramolecular transposition that can occur in the presence of magnesium ions.

In constructing a library, to achieve a 99% probability of complete coverage (i.e., an insert into each ORF) approximately 20,000 transposition events are required. The assumptions in this calculation are that transposition is truly random with respect to ORF target choice and that each ORF is the same size. Although Tn5 inserts have been found in all genes for which they have been sought, Tn5 does have target sequence biases that can skew the randomness in terms of gene distribution. There may also be unknown biases imposed on transposition by the condensation/organization of the nucleoid body. In addition, all ORFs are not the same size, but range in size in *E. coli*, for example, from under 100 codons to 2,383 codons. On the other hand, the results of synaptic complex electroporation/transposition described above represent inserts into dispensable functions only, since only viable colony forming units are formed. This clearly under represents the entire transposition insertion pool. Accordingly, to form a fully representative library, pools of between 50,000 and 500,000 viable transposition events should be sought. The invention described herein is sufficiently efficient to produce a library of this size.

SEQUENCE LISTING

<160> NUMBER OF SEQ ID NOS: 4

<210> SEQ ID NO 1
<211> LENGTH: 19
<212> TYPE: DNA
<213> ORGANISM: Transposon Tn5

<400> SEQUENCE: 1
ctgactctta tacacaagt                                                    19

<210> SEQ ID NO 2
<211> LENGTH: 19
<212> TYPE: DNA
<213> ORGANISM: Transposon Tn5

<400> SEQUENCE: 2
ctgtctcttg atcagatct                                                    19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Mosaic
      sequence between OE and IE sequences

<400> SEQUENCE: 3
ctgtctctta tacacatct                                                    19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:  Mosaic
      sequence between OE and IE sequences

<400> SEQUENCE: 4
ctgtctctta tacagatct                                                    19

The present invention is not intended to be limited to the foregoing, but to encompass all such variations and modifications as come within the scope of the appended claims.

vitro in a reaction that comprises magnesium ions at a level insufficient to support polynucleotide strand transfer.

We claim:

1. A method for making an insertional mutation at a random or quasi-random position in cellular nucleic acid in a target cell, the method comprising the step of:
introducing into the target cell a synaptic complex that comprises (a) a Tn5 transposase protein and (b) a polynucleotide that comprises a pair of nucleotide sequences adapted for operably interacting with Tn5 transposase to form a synaptic complex and a transposable nucleotide sequence therebetween, under conditions that mediate transpositions into the cellular nucleic acid.

2. A method as claimed in claim 1 wherein the method further comprises the step of:
combining the Tn5 transposase protein and the polynucleotide in vitro under conditions that disfavor polynucleotide strand transfer to form the synaptic complex.

3. A method as claimed in claim 2 wherein the Tn5 transposase protein and the polynucleotide are combined in 4. A method as claimed in claim 3 wherein the reaction lacks magnesium ions.

5. A method as claimed in claim 1 wherein the Tn5 transposase is a mutant Tn5 transposase modified relative to a wild type Tn5 transposase, the mutant transposase comprising:
a mutation at position 54; and
a mutation at position 372,
the mutant transposase having greater avidity for Tn5 outside end repeat sequences of a donor DNA and a lesser ability to form multimers than wild type Tn5 transposase.

6. A method as claimed in claim 5 wherein the mutation at position 54 is a substitution mutation.

7. A method as claimed in claim 6, wherein position 54 is a lysine.

8. A method as claimed in claim 5 wherein the mutation at position 372 is a substitution mutation.

9. A method as claimed in claim 8 wherein position 372 is a proline.

10. A method as claimed in claim 5 wherein the Tn5 transposase further comprises a substitution mutation at position 56, wherein the mutant transposase lacks an inhibitor activity.

11. A method as claimed in claim 10 wherein position 56 is alanine.

12. A method as claimed in claim 1 wherein the nucleotide sequence adapted for operably interacting with Tn5 transposase is an 18 or 19 base pair polynucleotide sequence that comprises nucleotide A at position 10, nucleotide T at position 11, and nucleotide A at position 12.

13. A method as claimed in claim 12 wherein the nucleotide sequence has the sequence 5'-CTGTCTCTTATACACATCT-3' (SEQ ID NO:3).

14. A method as claimed in claim 12 wherein the nucleotide sequence has the sequence 5'-CTGTCTCTTATACAGATCT-3' (SEQ ID NO:4).

15. A method for forming a synaptic complex between (a) a Tn5 transposase protein and (b) a polynucleotide that comprises a pair of nucleotide sequences adapted for operably interacting with Tn5 transposase to form a synaptic complex and a transposable nucleotide sequence therebetween, the method comprising the step of combining (a) and (b) in vitro under conditions that disfavor polynucleotide strand transfer to form the synaptic complex.

16. A method as claimed in claim 15 wherein the Tn5 transposase protein and the polynucleotide are combined in vitro in a reaction that comprises magnesium ions at a level insufficient to support polynucleotide strand transfer.

17. A method as claimed in claim 16 wherein the reaction lacks magnesium ions.

18. A method for forming a library of insertional mutations at random or quasi-random positions in cellular nucleic acid in a plurality of target cells, the method comprising the steps of:

introducing into the target cells a synaptic complex that comprises (a) a Tn5 transposase protein and (b) a polynucleotide that comprises a pair of nucleotide sequences adapted for operably interacting with Tn5 transposase to form a synaptic complex and a transposable nucleotide sequence therebetween, the transposable nucleotide sequence comprising a selectable marker, under conditions that mediate transpositions into the cellular nucleic acid; and screening for the cells that comprise the selectable marker.

* * * * *